United States Patent [19]

Garabedian

[11] Patent Number: Plant 5,856

[45] Date of Patent: Jan. 13, 1987

[54] GRAPE VINE

[76] Inventor: John M. Garabedian, 3104 E. Huntington Blvd., Fresno, Calif. 93702

[21] Appl. No.: 479,821

[22] Filed: Mar. 28, 1983

[51] Int. Cl.[4] ..... A01H 5/03
[52] U.S. Cl. ..... Plt./47
[58] Field of Search ..... Plt./47

*Primary Examiner*—R. E. Bagwill

*Attorney, Agent, or Firm*—Vergil L. Gerard

[57] ABSTRACT

Disclosed is a new and distinct grape vine broadly characterized by its berries which are greener in color, much larger, and with more cylindrical berries than the natural, ungibbrelled and ungirdled Thompson seedless grape which it most resembles, and by its early ripening date approximately one month before the natural Thompson seedless grape, its high sugar test and its low sugar-acid ratio.

1 Drawing Figure

The present invention relates to a grape vine and more particularly to a new and distinct variety thereof broadly characterized by its berries which are greener in color, much larger, and with more cylindrical berries than the natural, ungibbrelled and ungirdled Thompson seedless grape which it most resembles, and by its early ripening date approximately one month before the natural Thompson seedless grape, its high sugar test and its low sugar-acid ratio.

Although the instant variety most nearly resembles the Thompson seedless grape, it is distinguished therefrom and is an improvement thereon in that the instant variety is ripe for shipping approximately a month earlier than the Thompson seedless, and 15–20 days earlier than the Perlette.

Although the new variety originated as a mutation on a Dattier variety grape vine, it was discoverd by me in the summer of 1977 on a ranch owned by me in the San Joaquin Valley near Sanger, Calif. Sometime in the fall or winter of 1977 or early 1978, bud wood was taken from the mutated vine and budded over on a row of vines of another variety growing on my ranch near Fresno, Calif. The new variety thus asexually reproduced maintained the characteristics of the original mutation.

On July 22, 1980, all fruit of the new variety was ready for picking and had an average 17.3% sugar test and a sugar-acid ratio of 25.8:1. On the same date, fruit from the Thompson seedless variety grown on the same ranch had a 13.5% sugar test and a sugar-acid ratio of 13:1.

The fruit of the new variety was again tested on June 24, 1981. At that time 25% of the fruit was picking to eating ripe and had an average 15.4% sugar test and a sugar-acid ratio of 21.1:1. On the same date, fruit from the Perlette variety of grape vine grown near my ranch in Fresno, Calif., was tested and had an average 12.5% sugar test, and a sugar-acid ratio of 7.53:1.

The accompanying photo shows a characteristic cane section of the subject grape vine and clusters of the mature fruit, and shows the characteristics thereof. All major color plate identifications are by reference to Maerz and Paul's Dictionary of Color, 1st Ed.

DESCRIPTION

Vine

General: Medium size, vigorous, horizontal canes, hardy and productive.

Trunk: Small and slender.

Bark: Adherent; adhering straps are light gray in color.

Canes: Long to medium; numerous, medium slender; yellow to green, straight and flat. Average 18 canes per vine.

Nodes: Slightly enlarged, flattened.

Internodes: Longest canes, 9, 10, 11, 12; shortest canes, 1, 2, 3, 4, 5; medium to short.

Tendrils: Intermittent, slender, medium length, mostly bifurcated, smooth, few in number.

Bloom: Early, fertile bloom. First bloom, May 4, 1981, full bloom, May 14, 1981. Five percent bloom on May 7, 1981. Upright stamens.

Leaves

Size, shape: Mostly medium size, many small, few large. Average width×length=141 sq.cm; cordate, thin.

Upper surface: Dark green — 23 J-9 Polo Green; glossy, medium smooth, mostly "plane".

Lower surface: Pale green — 21 K-8 Fern Green; slightly cob-webby.

Lobes: Five in number, mostly obtuse, few acuminate.

Petiolar sinus: Shallow, wide.

Basal sinus: Medium deep to shallow, narrow.

Lateral sinus: Deep, narrow.

Margin: Dentate.

Teeth: Number 46–70. Medium deep, narrow.

Fruit

Ripening: The fruit is described on July 22, 1980. All fruit could have been picked at this time for Eastern shipment. On June 24, 1981, 25% is ripe for shipping or eating, which is very early season for the area, and, in general, fruit ripens 15–20 days before the Perlette grape. It is of good keeping and shipping quality.

Cluster: Mostly medium size, a few large, a few small; long to medium length, medium slender size, tapering to cylindrical shape, mostly regular shape, loose to medium compact. Nineteen bunches of clusters on random selected vine, weight 6 oz. to 1 lb. 2 oz.

Berry: Average size, 17 mm long×14 mm wide. Medium adherent shells, mostly medium size, few small;

variable, slightly cylindrical form; light green color with thin bloom.

Skin: Medium thick, medium tender; separates from pulp easily.

Flesh: Greenish color, meaty, tender, juicy, clear, sweet — sprightly.

Quality: Very good.

Seeds: Residual seed trace in most berries.

Use: Dessert, market, home, raisin, wine.

Having thus described a new grape vine, what is claimed is:

1. A new and distinct variety of grape vine substantially as illustrated and described and being characterized by its early maturity, approximately one month earlier than the Thompson seedless grape variety; by berries which are greener in color than the Thompson seedless grape at similar conditions of ripening; by berries larger and more cylindrical than the natural ungibbrelled and ungirdled Thompson seedless grape berries at similar conditions of ripening; and by some berries having a residual seed trace.

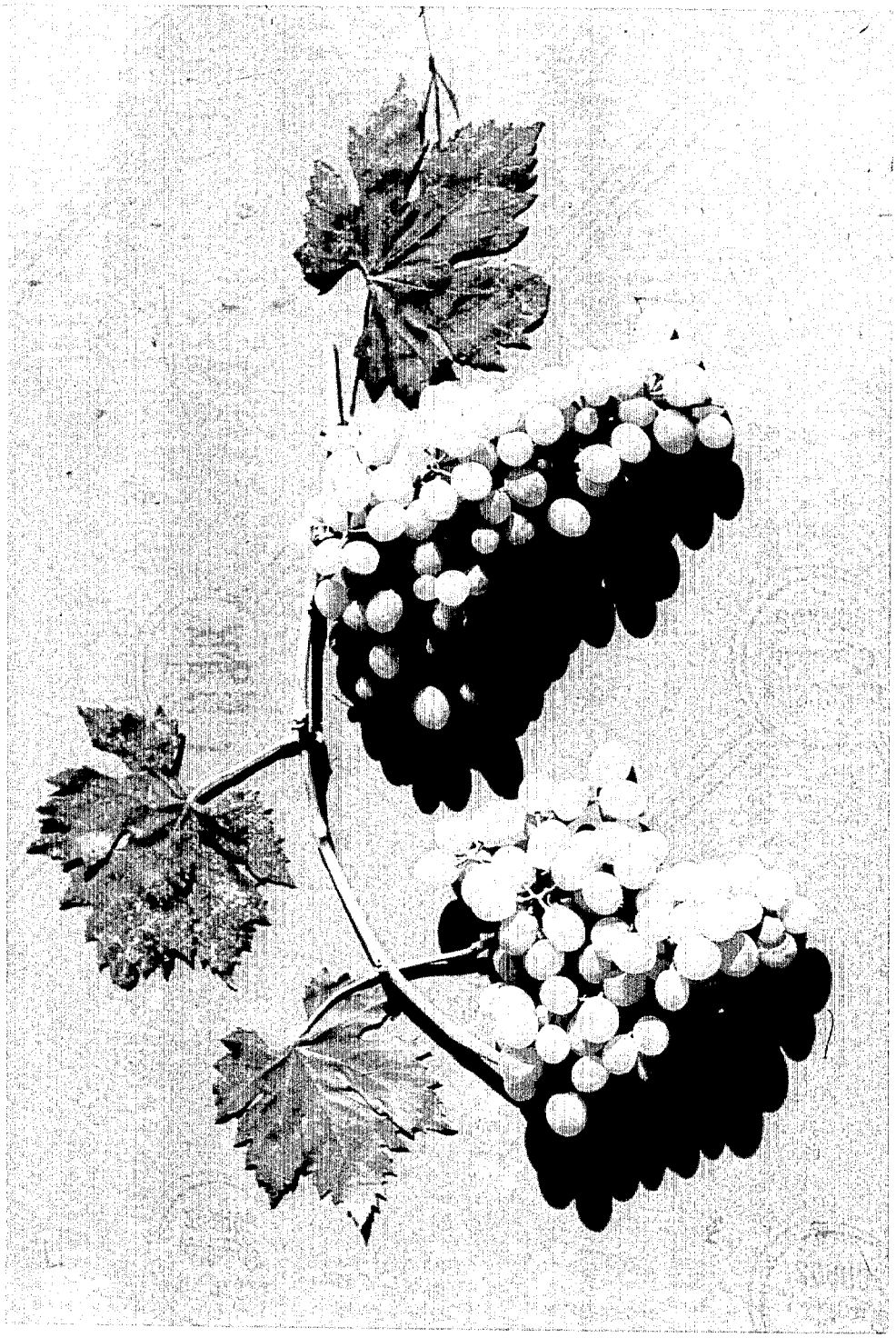

* * * * *